(12) United States Patent
Schiller

(10) Patent No.: US 6,231,849 B1
(45) Date of Patent: May 15, 2001

(54) SIMULATED SEMINAL FLUID

(75) Inventor: George A. Schiller, 17 Ridgeview Ter., Goshen, NY (US) 10924

(73) Assignees: George A. Schiller; Jonathan G. Schiller

( * ) Notice: Subject to any disclaimer, the term of this patent is extended or adjusted under 35 U.S.C. 154(b) by 0 days.

(21) Appl. No.: 09/276,227

(22) Filed: Mar. 25, 1999

(51) Int. Cl.[7] .......................... A01N 43/36; A01N 25/00; A01M 31/00; A01M 31/06
(52) U.S. Cl. ..................... 424/84; 424/405; 424/545; 424/546; 514/423; 514/428; 514/408; 43/1
(58) Field of Search ................. 424/84, 405, 545, 424/546; 514/423, 428, 408; 43/1

(56) References Cited

U.S. PATENT DOCUMENTS

| | | | |
|---|---|---|---|
| 2,959,354 | 11/1960 | Beck | 239/36 |
| 3,046,192 | 7/1962 | Bilyeu | 239/9 |
| 3,119,650 | 1/1964 | Bilyeu | 422/125 |
| 4,213,875 | 7/1980 | Isbell | 424/84 |
| 4,302,899 | 12/1981 | DeHart | 43/1 |
| 4,667,430 | 5/1987 | Ziese, Jr. | 43/1 |
| 4,818,535 | * 4/1989 | Baines et al. | 424/407 |
| 4,944,940 | 7/1990 | Christenson, II | 424/84 |

\* cited by examiner

*Primary Examiner*—John Pak
(74) *Attorney, Agent, or Firm*—Joseph L. Spiegel

(57) ABSTRACT

The simulation of mammalian male reproductive secretions or seminal fluids by specific odoriferous chemical compounds comprised of 1-Methyl Pyrrolidine, 1-Methyl-2-Pyrrolidine Methanol, 1-Methyl-2 Pyrrolidine Ethanol, Pyrrolidine and 2-Pyrrolidone either alone or in various combinations with one another. The simulated seminal fluid's novel odor and appearance is enhanced by the incorporation of various thickeners, suspending agents, solvents, coloring agents, preservatives and surfactants.

17 Claims, No Drawings

SIMULATED SEMINAL FLUID

BACKGROUND OF THE INVENTION

1. Field of the Invention

This invention relates to the development of novel sexual odors of male mammalian origin and to the specific odorants, materials and chemicals used to simulate seminal fluid odor and appearance. This odorant and chemical composition is designed to simulate mammalian male reproductive secretions i.e.: the penile ejaculate comprising a viscid fluid containing spermatozoa; a mixture produced by secretions of the testes, seminal vesicles, prostrate and bulbouretheral glands hereafter collectively referred to as seminal fluids.

2. Description of the Prior Art

Deer and other big game hunters have for decades sought out and employed specific odors and scents that, when utilized by the hunter while pursuing game, will enhance their chances of successfully harvesting the game animal. Typically, these odors and scents which may be entirely natural or synthetic in origin or in any combination thereof to date have been oriented toward attracting or distracting big game animals' senses of smell by appealing to their sense of desire for food, of herding, of curiosity, and of social and sexual awareness and breeding.

Specific examples in these areas are: 1) Commercial deer and other big game animal feeds and mineral supplements, food lures and scents such as acorn, alfalfa, apple, beechnut, birch buds, cabbage, carrot, cedar, clover, corn, honeysuckle, peanut, persimmon, pine, wild grape; 2) Commercial curiosity lures and scents such as anise, banana, berry, caramel, citrus, coconut, honey, maple, molasses, rum, wintergreen and vanilla; and, 3) Commercial deer and other big game animal lures and scents such as natural and/or synthetic musk compounds, tarsal glands, interdigital glands, preorbital glands, commercial buck lures and scents, commercial doe in heat/estrus lures and scents, fawn, buck, doe, doe in heat/estrus urines, etc.

SUMMARY OF THE INVENTION

A feature of this invention relates to the breeding period of male mammalian big game animals and how reproductive odors associated with the storage and ejaculation of their sperm and seminal fluids occur at this time period (often referred to as the rutting period when the male of the species actively pursues the female of the species for the specific purpose of mating and reproducing the species). The odors emanating from the male's seminal fluid is unique and novel and it is the purpose of this invention to simulate these odors and their related appearance for the purpose of employing them in a suitable medium, to act as a sexually stimulating scent to attract big game animals and to assist the hunter in pursuing and harvesting big game animals. The seminal fluid odors may also be employed as a curiosity scent to attract other adult and juvenile male and female members of the species to within suitable range for harvesting by the hunter. In addition, the seminal fluid odors can also be used as a masking agent that will cover or over-ride human odors and other foreign odors that alarm big game animals. The seminal fluid odors are ideally employed during the rutting period but can also be successfully used to harvest big game animals both before and after the rutting period.

DESCRIPTION OF THE PREFERRED EMBODIMENT

I have found that specific chemical compounds herein identified as, 1-Methyl Pyrrolidine, molecular formula C5H11N, formula weight 85.15, 1-Methyl-2-Pyrrolidine Methanol, molecular formula C6H13NO, formula weight 115.18 also known as 1-Methyl Pyrrolidin-2-Methanol, 1-Methyl-2-Pyrrolidine ethanol, molecular formula C7H15NO, formula weight 129.20 also known as 1-Methyl Pyrrolidine-2 Ethanol, Pyrrolidine, molecular formula C4H9N, formula weight 71.12 also known as Azacyclopentane, Azolidine, Prolamine, Pyrrole Tetra HydroPyrrolidine, Pyrrolidin, Tetra Hydropyrrole, and Tetramethylenime, and 2-Pyrrolidone, molecular formula C4H7NO formula weight 85.11 also known as 2-Pyrrolidinone and Butyrolactam, alone or in combination with one another to simulate the seminal fluid odor of male mammals. Chemical structures for these identified compound are represented as follows:

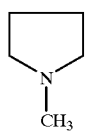
METHYL PYRROLIDINE

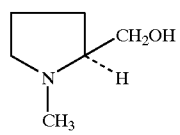
1 METHYL-2-PYRROLIDINE METHANOL

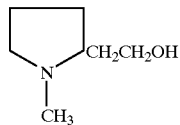
1 METHYL-2-PYRROLIDINE ETHANOL

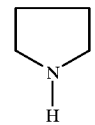
PYRROLIDINE

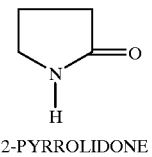
2-PYRROLIDONE

1-Methyl Pyrrolidine, 1-Methyl-2-Pyrrolidine Methanol, 1-Methyl-2-Pyrrolidine Ethanol, Pyrrolidine and 2-Pyrrolidone either alone or in various combinations or any of its synonyms either alone or in various combinations are ideally employed in a suitable medium consisting of an appropriate amount of water and/or other designated solvents or dilutives, suspending and/or thickening agents, coloring agents, surfactants and preservatives if required, at levels ranging from 0.01%/wt to 30.00%/wt. However, if a more concentrated level of seminal fluid odor is required, the aforementioned chemicals may be employed at full strength alone or in various combinations with one another or in conjunction with other aspects of this invention, providing accompanying health and safety precautions are observed.

The seminal fluid odor and appearance can accompany a variety of physical forms for employment in the pursuit and harvesting of big game animals and for other personnel as later stated herein. Among these various physical forms are liquids, gels, ointments, emulsions and powders. The seminal fluid preferred medium is a water/propylene glycol mixture, which has been thickened to the appropriate viscosity with commercial thickening and/or suspending agents. To further enhance the deer and other big game attracting capabilities of this invention, a portion of the water base medium may be comprised of deer or other big game urine in whatever amount so desired. Since the bulk constituent of urine is water, a full replacement of the water portion of the medium can be achieved. Specifically, this urine is ideally obtained from deer and may consist of buck urine, doe urine, doe in heat urine, alone or in combination with one another. Depending on the availability of the aforementioned urine, other big game animal urine such as elk, moose, goat, and sheep urine can be substituted. Urine obtained from domesticated or captivated animals such as cows, bulls, horses, pigs, goats, buffalo, etc. may also be employed if so desired. An appropriate yellowish off white coloring system may also be employed to impart to the final mixture the appearance and consistency of mammalian seminal fluid. Depending on the particular materials chosen for the aforementioned aqueous based medium; a commercial preservative and surfactant may also be employed. Among the other suitable materials besides water and propylene glycol that may be employed in the medium, I have found that ethylene, diethylene, dipropylene, triethylene, tetraethylene, polyethylene, butylene, paramethylene, and hexylene glycols, methanol, ethanol and glycerol, in whatever amount is required to achieve the desired degree of solvency, viscosity and freezeproofness may also be used.

I have also found that the following thickening and suspending agents will give the aqueous based medium a viscosity that simulates seminal fluid. Suitable agents to achieve this viscosity may include: Acrylic Acid Polymers, Alginate, Carboxy Methyl Cellulose, Carrageenan, Dextrin, Ester Gum, Ethyl Cellulose, Gelatin, Guar Gum, Gum Arabic, Gum Ghatti, Gum Karaya, Gum Tragacanth, Hydroxy ethyl cellulose, Hydroxypropyl Methylcellulose, Locust Bean Gum, Malto Dextrin, Methyl Cellulose, Micro Crystalline Cellulose, Pectin, Pysilium, Sodium Alginate, Sodium Carboxy Methyl Cellulose, Sodium Silicate, Potato, Rice, Sage, Arrowroot and Wheat Starch, and Xanthan Gum in whatever amount is required to achieve the desired consistency.

I have also found that the following materials and coloring agents will impart to the aqueous based medium, a color that simulates seminal fluid: Aluminum and Zinc Oxide, Aluminum and Magnesium Hydroxide, Aluminum, Calcium and Magnesium Silicate, Sodium Silicate, Annatto, Beta Carotene, Brominated Vegetable Oil, Cadmium Oxide, Calcium, Magnesium and Zinc Carbonate, Calcium, Magnesium and Zinc Phosphate, Calcium Oxalate, Calcium, Potassium, Sodium and Zinc Caseinate; Calcium, Magnesium, Potassium, Sodium and Zinc Stearate; Magnesium and Sodium Aluminate; Saffron, Silicon Dioxide, Sodium Aluminum Silicate; Talc, Tartrazine (Yellow #5), Titanium Dioxide, Tumeric, Yellow Iron Oxide Pigment Dispersions, Zinc Oleate and Zinc Pyrophosphate in whatever amount or combination is required to achieve the desired color.

I have also found that the following antimicrobials, antioxidants and preservatives will, depending upon the particular choice of the thickening and/or suspending agents, prevent the deterioration of the aforementioned agents. They include 1, 2, Benzisothiazolin-3-one, Benzoic Acid, Benzyl Bromoacetate, Butyl Paraben, Butylated Hydroxy Anisole (BHA), Butylated Hydroxy Toluene (BHT), Calcium Propionate, 1-(3-Chloroallyl) 3, 5, 7, Triaza-1-Azoniaadamantane Chloride, Diazolidinyl Urea, Ethyl Paraben, Hexahydro-2, 3, 5 Triethyl-S-Triazine, Imidazolidinyl Urea, 3-iodo-2-propynyl Butylcarbamate, Methyl Chloroisothiazoline, Methyl Isothiazoline, Methyidibromo Glutaronitrile, Methyl Paraben, Potassium Benzoate, Potassium Lactate, Potassium Sorbate, Phenoxyethanol, Propyl Gallate, Propyl Paraben, Sodium Benzoate, Sodium Diacetate, Sodium Hydroxymethylglycinate, Sodium Lactate, Sodium Lauryl Sulfate, Sodium Nitrite, Sodium Propionate, Sorbic Acid, and Tertiary Butyl Hydroquinone (TBHQ) in whatever amount is required to achieve the desired degree of preservation.

A further feature of the present invention resides in the provision that it may contain a surfactant or wetting agent, the purpose of which is to increase the rate of evaporation by reducing the surface tension of the aqueous based medium and to solubilize other odiferous components that may be included to enhance the seminal fluid odor. The amount of surfactant would normally be small but larger amounts could be employed to also increase the viscosity of the seminal fluid.

I have also found that the following surfactants are capable of performing the aforementioned functions: Benzene Alkyl Sulfonate, Octyl and/or Nonylphenoxypoly (2-12) ethylene oxyethanol. Octylphenoxypolyethoxyethanol, Sodium Dioctylsulfosuccinate, Triethanolamine Dodecylbenzenesulfonate, in whatever amount is required to achieve the desire effect.

I have also found that the seminal fluid odor and color can be incorporated into gels, emulsions, and ointments if so desired. The seminal fluid odor in this type of chemical composition would have a slower rate of dispersion into the air due to the surface tension of the medium but would have the advantage of lasting longer during employment. The aqueous or nonaqueous gelling agents either alone or in combination with one another can include the aforementioned coloring agents and preservatives as required. Suitable gelling agents may include: Acrylic Acid Polymers, Carrageenan, Carboxymethylcellulose, Ethyl Cellulose, Gelatin, Hydroxethyl Cellulose, Hydroxyl Propylmethyl Cellulose, Methyl Cellulose, Microcrystalline Cellulose, Mineral oil (and) Hydrogenated Butylene/Ethylene/Styrene Copolymer (and) Hydrogenated Ethylene/Propylene/Styrene Copolymer, Pectin, Petrolatum, Petrolatum and Mineral Oil Blends, Petrolatum and Vegetable Oil Blends, Sodium Carboxymethyl Cellulose and Sodium Petroleum Sulfonates in whatever amount is required to achieve the desired effect.

I have also found that the seminal fluid odor and color can be incorporated into a variety of bulk or base powders if so desired. The seminal fluid odor in this type of chemical composition would be plated or sprayed onto or otherwise applied to any of the aforementioned coloring agents and/or to a variety of suitable absorbing materials which would retain the odor and over a period of time be released or dispersed into the air to attract big game animals. The seminal fluid odor may be added to a small portion of the coloring agents, base powders and/or absorbing materials mixed thoroughly and then introduced to any remaining coloring agents or absorbing material and fully mixed. Suitable agents to employ in a powder medium may include: Aluminum and Zinc Oxide, Aluminum and Magnesium Hydroxide, Aluminum, Calcium and Magnesium Silicate, Annatto, Cadmium Oxide, Calcium, Magnesium and Zinc Carbonate, Calcium, Magnesium, Sodium and Zinc Phosphate, Calcium Oxalate, Calcium, Potassium, Sodium and Zinc Caseinate, Calcium, Magnesium, Potassium, Sodium and Zinc Stearate, Magnesium Aluminum Silicate, Magnesium and Sodium Aluminate, Salt, Silicon Dioxide, Sodium Tripolyphosphate, Sodium Alumino Silicate, Starch, Sugar, Talc, FD&C Yellow #5 Lake, Titanium Dioxide, Tumeric, Yellow Iron Oxide, Zinc Oleate and Zinc Pyrophosphate in whatever amount that is required to achieve the desired effect.

I have also found that the odor and appearance of the seminal fluid can be employed in an emulsion physical form, if so desired.

The following emulsifying agents will, at the proper amount, give the medium a viscosity that simulates seminal fluid. The emulsifying agents when employed in an aqueous base either alone or in combination with one another will prevent the aforementioned odiferous materials from separating and will also hold the aforementioned coloring agents in an emulsion form and also prevent physical separation of the components. These emulsifying agents require aqueous compatible preservatives, which may be obtained by the employment of the proper aforementioned preservatives. Suitable emulsifying agents may include Alginate, Ester Gum, Gelatin, Guar Gum, Gum Arabic, Gum Ghatti, Gum Karaya, Gum Tragacanth, Locust Bean Gum, Malto Dextrin, Pectin, Psyllium, Starch and Xanthan Gum in whatever amount is required to achieve the desired effect.

The seminal fluid may be employed by hunters as an aid in the pursuit an harvesting of various species of big game animals, by nature and wildlife photographers who have to come in close proximity to wildlife in order to photograph, various state and government conservation personnel who need to attract or capture animals for such purposes as health checks, disease control, reproductive measurements, etc. and for personnel involved with game animal population control and relocation programs.

The seminal fluid may be contained and transported in a wide variety of containers such as glass, polyethylene, polyvinyl chloride, polypropylene, styrene, suitable lined metal containers, aerosol containers, etc. The seminal fluid may be employed in a variety of ways, the simplest being to merely dispense an appropriate quantity on surrounding rocks, trees, branches, leaves, twigs, or any other surfaces that will minimally absorb the seminal fluid and thereby prevent or retard it from fully disseminating into the air. Other means of dispersing the seminal fluid could also include the use of commercial scent vents in which the seminal fluid is absorbed onto a suitable medium such as cotton or felt and subsequently released into the air by unscrewing or removing the cap of the scent vent. The seminal fluid may also be applied to the hunters' footwear to leave a trail for the game animals to follow or it may be applied to a rope or other similar absorbing material and dragged through he brush to lay a scent trail for game animals to follow. Deer and other big game animals are known to communicate by vocal and odiferous means and are well aware of one anothers' presence even though at times they are not in audible or visual contact by the odors they produce. These odors originate from such glands as the tarsal, metatarsal, interdigital, preorbital, and odors produced during ovulation and copulation. These odors are principal means of communicating with other deer and gives them the ability to locate one another, to form herds and for protection, socialization, feeding and for various other purposes and to propagate the species.

Substantial field testing of the effectiveness of the invention's simulated seminal fluid's odor to attract deer was carried out under a wide variety of weather and temperature conditions. These conditions varied from a low of 15° F. to a high of 90° F. and included periods of drizzle, rain, snow and sunshine. Wind velocities ranged from "dead calm" to winds in the 30–40 MPH range. Farmland and heavily wooded areas that were known to contain both mature and young whitetail deer of both sexes were chosen for the actual test site. The seminal fluid was employed in varying amounts (¼ teaspoon to 1 tablespoon) on surrounding rocks, trees, branches, leaves, etc. and at varying heights and located at the 4 compass points approximately 10–20 yards away from the actual location of the hunter. A quantity of seminal fluid compound was also used adjacent to the hunter to serve not only in further attracting deer but to overcome human odors. This disbursement was designed to prevent deer from honing in and identifying the exact source of the seminal fluid thereby giving the hunter an increased chance of harvesting the deer before being detected.

The actual testing periods can be grouped into three somewhat overlapping periods; prerut, rut and postrut periods. During the prerut period, the seminal fluid odor was observed to have a curiosity effect on adult male and female deer. Adult deer, often accompanied by yearling or younger deer, were observed after smelling the seminal fluid odor to continually sniff the air to detect the exact source of the odor. It was apparent that the seminal fluid's reproductive odor was familiar to them and therefore not uncommon nor alarming. It is also known that deer have an inherent herding instinct and after smelling the seminal fluid odor knew other deer were in the vicinity and thereby attempting to seek them out. During the rutting period when seminal fluid odor is frequently common in the air, it was observed that adult deer of both sexes were attracted to the odor. In rut, adult male deer with swollen necks and flared nostrils were observed rushing into the test site obviously looking forward to encountering a female deer in heat to mate with or to located and fight with another male deer that had encroached upon his breeding territory. Female deer either alone or in small groups of other female deer were observed to react to the seminal fluid odor with interest and curiously. It was apparent that they considered the seminal fluid a commonly encountered odor during the rutting period and did not at all become alarmed or panicked. It is believed that the seminal fluid odor indicated to the deer that other deer were also in the vicinity and therefore no reason to be alarmed. During the postrut period, the seminal fluid odor still had a curiosity effect on mature male and female deer. Essentially, the same observations were made at this period as compared to the prerut period. Adult and yearling deer were observed after smelling the seminal fluid odor to continually sniff the air to detect the source of the odor. Again, it is strongly believed that the seminal fluids reproductive odor was still familiar to them from the very recent breeding or rut period and therefore not alarming. The tendency for individual deer, after detecting the seminal fluid odor was to seek out the odor in anticipation of joining or herding or breeding with other deer. During all these periods, it was discovered that the optimum placement of the seminal fluid was at a height of 3–10 feet above ground level and on any surface that would minimally absorb the seminal fluid and prevent or limit its dispersion into the air. Under average wind conditions these heights adequately dispersed the seminal fluid odor in the wind currents for deer to detect and consequently be attracted to.

In summation, it was observed that the simulated seminal fluid had, during the prerut, and postrut periods, a curiosity effect on deer and at no time alarmed or panicked them. The odor was recognized as not being uncommon and related to other deer being in the vicinity. During the rut period, male deer were observed to become very aggressive after detecting the seminal fluid odor to the point of blindly charging into the test site in an attempt to locate the exact source of the odor. The invention can therefore be employed to successfully harvest big game animals during the prerut, rut and postrut periods. However, the particular rutting period for big game animals indicated the highest degree of attraction to the male of the species.

What is claimed is:

1. A chemical composition that simulates the odor and appearance of male mammalian seminal fluid secretion that includes an odiferous portion selected from the group consisting of 1-methyl pyrrolidine, 1-methyl-2-pyrrolidine methanol, 1-methyl-2-pyrrolidine ethanol, pyrrolidine, and 2-pyrrolidone, thickener, suspending agent, solvent, surfactant, coloring agent and preservative, the odiferous portion comprising 0.25 to 80.00% by weight of the composition.

2. The composition of claim 1 wherein the solvent includes a mixture selected from the group consisting of propylene glycol, ethylene glycol, diethylene glycol, dipropylene glycol, triethylene gylcol, tetra ethylene glycol, polyethylene glycol, butylene glycol, paramethylene glycol, hexylene glycol, methanol, ethanol and glycerol, the mixture comprising 1.00 to 99.0%, by weight of the composition.

3. The composition of claim 2 wherein the thickening agent is selected from the group consisting of acrylic acid polymers, alginate, carboxy methyl cellulose, carrageenan, dextrin, ester gum, ethyl cellulose, gelatin, guar gum, gum arabic, gum ghatti, gum karaya, gum tragacanth, hydroxy ethyl cellulose, hydroxy propyl cellulose, locust bean gum, malto dextrin, methyl cellulose, micro crystalline cellulose, pectin, psyllium, sodium alginate, sodium carboxy methyl cellulose, sodium silicate, potato starch, rice starch, sage starch, arrowroot starch, wheat starch and xanthan gum, the thickening agent comprising 0.10 to 90.00%, by weight of the composition.

4. The composition of claim 3 wherein the coloring agent is selected from the group consisting of aluminum oxide, zinc oxide, aluminum hydroxide, magnesium hydroxide, aluminum silicate, calcium silicate, magnesium silicate, sodium silicate, annatto, beta carotene, brominated vegetable oil, cadmium oxide, calcium carbonate, magnesium carbonate, sodium carbonate, zinc carbonate, calcium phosphate, magnesium phosphate, sodium phosphate, zinc phosphate, calcium oxalate, calcium caseinate, potassium caseinate, sodium caseinate, zinc caseinate, calcium stearate, magnesium stearate, potassium stearate, sodium stearate, zinc steareate, magnesium aluminate, sodium aluminate, saffron, silicon dioxide, sodium aluminum silicate, talc, tartrazine (Yellow #5), titanium dioxide, tumeric, yellow iron oxide pigment dispersions, zinc oleate and zinc pyrophosphate, the coloring agent comprising 0.01 to 25.00% by weight of the composition.

5. The composition of claim 4 wherein the preservative is selected from the group consisting of 1, 2 benzisothiazolin-3-one, benzoic acid, benzyl bromoacetate, butyl paraben, butylated hydroxy anisole (BHA), butylated hydroxy toluene (BHT), calcium propionate, 1-(3-chloroallyl) 3, 5, 7, triaza-1-azoniaadamantane chloride, diazolidinyl urea, ethyl paraben, hexahydro-2, 3, 5 triethyl-s-triazine, imidazolidinyl urea, 3-iodo-2-propynyl butylcarbamate, methyl chloroisothiazoline, methyl isothiazoline, methyldibromo glutaronitrile, methyl paraben, potassium benzoate, potassium lactate, potassium sorbate, phenoxyethanol, propyl gallate, propyl paraben, sodium benzoate, sodium diacetate, sodium hydroxymethylglycinate, sodium lactate, sodium lauryl sulfate, sodium nitrite, sodium propionate, sorbic acid, and tertiary butyl hydroquinone, the preservative comprising 0.02 to 3.00% by weight of the composition.

6. The composition of claim 5, including a surfactant selected from the group consisting of benzene alkyl sulfonate, octyl and/or nonylphenoxypoly (2–12) ethylene oxyethanol, octylphenoxypolyethoxyethanol, sodium dioctylsulfosuccinate and triethanolamine dodecylbenzenesulfonate, the surfactant comprising 0.02 to 5.00% by weight of the composition.

7. The composition of claim 1 including a non-aqueous based medium selected from the group consisting of avocado oil, canola oil, castor oil, coconut oil, corn oil, and cottonseed oil, glyceryl triacetate, mineral oil, neatsfoot oil, olive oil, palm oil, peanut oil, rapeseed oil, safflower oil, sesame oil, soya bean oil, sunflower oil, tallow oil and vegetable oil, diethyl malonate, dimethyl phthalate, diethyl phthalate, dibutyl phthalate, di-(2 ethylhexyl) phthalate, ethylhexyl phthalate, di-(2 ethylhexyl) terephthalate, diethyl sebacate, diethyl succinate, petrolatum, silicone and tripropinin, the non-aqueous based medium comprising 1.0% to 99.0% by weight of the composition.

8. The composition of claim 7 wherein the coloring agent is selected from the group consisting of aluminum oxide, zinc oxide, aluminum hydroxide, magnesium hydroxide, aluminum silicate, calcium silicate, magnesium silicate, sodium silicate, annatto, beta carotene, brominated vegetable oil, cadmium oxide, calcium carbonate, magnesium carbonate, sodium carbonate, zinc carbonate, calcium phosphate, magnesium phosphate, sodium phosphate, zinc phosphate, calcium oxalate, calcium caseinate, potassium caseinate, sodium caseinate, zinc caseinate, calcium stearate, magnesium stearate, potassium stearate, sodium stearate, zinc stearate, magensium aluminate, sodium aluminate, saffron, silicon dioxide, sodium aluminum silicate, talc, FD&C yellow #5 lake, titanium dioxide, tumeric, yellow iron oxide pigment dispersions, zinc oleate and zinc pyrophosphate, the coloring agent comprising of 0.01 to 25.00% by weight of the non-aqeous composition.

9. The composition of claim 8 wherein the preservative is selected from the group consisting of butylated hydroxy anisole (BHA), butylated hydroxy toluene (BHT), propyl gallate and tertiary butyl hydroquinone (TBHQ), the preservative comprising 0.02% to 2.00% by weight of the composition.

10. The composition of claim 1 including a material which will impart the consistency and viscosity of a gel or ointment selected from the group consisting of acrylic acid polymer, carrageenan, carboxymethyl cellulose, ethyl cellulose, gelatin, hydroxyettiyl cellulose, hydroxypropylmethyl cellulose, methyl cellulose, microcrystalline cellulose, mineral oil (and) hydrogenated butylene/ethylene/styrene copolymer (and) hydrogenated ethylene/propylene/styrene copolymer, pectin, petrolatum, petrolatum and mineral oil blends, petrolatum and vegetable oil blends, sodiumcarboxymethyl cellulose ant sodium petroleum sulfonates, the material comprising 1.00 to 99.0% by weight of the composition.

11. The composition of claim 10 wherein the coloring agent is selected from the group consisting of aluminum oxide, zinc oxide, aluminum hydroxide, magnesium hydroxide, aluminum silicate, calcium silicate, magnesium silicate, sodium silicate, annatto, beta carotene, brominated vegetable oil, cadmium oxide, calcium carbonate, magnesium carbonate, sodium carbonate, zinc carbonate, calcium phosphate, magnesium phosphate, sodium phosphate, zinc phosphate, calcium oxalate, calcium caseinate, potassium caseinate, sodium caseinate, zinc caseinate, calcium stearate, magnesium stearate, potassium stearate, sodium stearate, zinc stearate, magnesium aluminate, sodium aluminate, saffron, silicon dioxide, sodium alumnium silicate, talc, tartrazine (yellow #5), titanium dioxide, tumeric, yellow iron oxide pigment dispersions, zinc oleate and zinc pyrophosphate, the coloring agent comprising 0.01 to 25.00% by weight of the composition.

12. The composition of claim 11 wherein the preservative is selected from the group consisting of 1,2 benzisothiazolin-3-one, benzoic acid, benzyl bromoacetate, butyl paraben, butylated hydroxy anisole (BHA), butylated hydroxy toluene (BHT), calcium propionate, 1-(3-chloroallyl) 3, 5, 7, triaza-1-azoniaadamantane chloride, diazolidinyl urea, ethyl paraben, hexahydro-2, 3, 5 triethys-s-triazine, imidazolidinyl urea, 3-iodo-2-propynly butylcarbamate, methyl chloroisothiazoline, methly isothiazoline, methyldibromo glutaronitrile, methyl paraben, potassium benzoate, potassium lactate, potassium sorbate, phenoxyehtanol, propyl gallate, propyl paraben, sodium benzoate, sodium diacetate, sodium hydroxymethylglycinate, sodium lactate, sodium lauryl sulfate, sodium nitrite, sodium propionate, sorbic acid, and tertiary butyl hydroquinone (TBHQ), the preservative comprising 0.02 to 3.00% by weight of the composition.

13. The composition of claim 1 including a base or absorbing medium, which will impart the consistency of a powder, the medium selected from the group consisting of aluminum oxide, zinc oxide, aluminum hydroxide, magnesium hydroxide, annatto, cadmium oxide, calcium carbonate, magnesium carbonate, sodium carbonate, zinc carbonate, calcium phosphate, magnesium phosphate, sodium phosphate, zinc phosphate, calcium oxalate, calcium caseinate, potassium caseinate, sodium caseinate, zinc caseinate, calcium stearate, magnesium stearate, potassium stearate, sodium stearate, zinc stearate, magnesium aluminate, sodium aluminate, salt, silicon dioxide, sodium tripolyphosphate, sodium aluminum silicate, starch, sugar, talc, FD&C yellow #5 lake, titanium dioxide, tumeric, yellow iron oxide, zinc oleate and zinc pyrophosphate, the medium comprising 80.0 to 98.0% by weight of the composition.

14. The composition of claim 2 including a stabilizing thickening agent selected from the group consisting of alginate, ester gum, gelatin, guar gum, gum arabic, gum ghatti, gum karaya, gum tragacanth, locust bean gum, maltodextrin, pectin, psyllium, starch and xanthan gum, the stabilizer comprising 1.0 to 30.0% by weight of the composition.

15. The composition of claim 14 wherein the coloring agent is selected from the group consisting of Aluminum Oxide, Zinc Oxide, Aluminum Hydroxide, Magnesium Hydroxide, Aluminum Silicate, Calcium Silicate, Magnesium Silicate, Sodium Silicate, Annatto, Beta Carotene, Brominated Vegetable Oil, Cadmium Oxide, Calcium Carbonate, Magnesium Carbonate, Sodium Carbonate, Zinc Carbonate, Calcium Phosphate, Magnesium Phosphate, Zinc Phosphate, Calcium Oxalate, Calcium Caseinate, Potassium Caseinate, Sodium Caseinate, Zinc Caseinate, Calcium Stearate, Magnesium Stearate, Potassium Stearate, Sodium Stearate, Zinc Stearate, Magnesium Aluminate, Sodium Aluminate, Saffron, Silicon Dioxide, Sodium Aluminum Silicate, Talc, Tartrazine (Yellow #5), Titanium Dioxide, Tumeric, Yellow Iron Oxide Pigment Dispersions, Zinc Oleate and Zinc Pyrophosphate, the coloring agent comprising 0.01 to 25.00% by weight of the composition.

16. The composition of claim 15 wherein the preservative is selected from the group consisting of the following: 1,2 Benzisothiazolin-3-one, Benzoic Acid, Benzyl Bromoacetate, Butyl Paraben, Butylated Hydroxy Anisole (BHA), Butylated Hydroxy Toluene (BHT), Calcium Propionate, 1-(3-Chlorallyl) 3,5,7, Triaza-1-Azoniaadamantane Chloride, Diazolidinyl Urea, Ethyl Paraben, Hexahydro-2,3,5 Triethyl-S-Trazine, Imidazolidinyl Urea, 3-iodo-2-propynyl Butylcarbamate, Methyl Chloroisothiazoline, Methyl Isothiazoline, Methyidibromo Glutaronitrile, Methyl Paraben, Potassium Benzoate, Potassium Lactate, Potassium Sorbate, Phenoxyethanol, Propyl Gallate, Propyl Paraben, Sodium Benzoate, Sodium Diacetate, Sodium Hydroxymethylglycinate, Sodium Lactate, Sodium Lauryl Sulfate, Sodium Nitrate, Sodium Propionate, Sorbic Acid, and Tertiary Butyl Hydroquinone (TBHQ), the preservative comprising 0.02 to 3.00% by weight of the composition.

17. The composition of claim 6 including animal urine to further enhance the deer attracting capability of the composition, the animal urine selected from the group consisting of deer buck urine, doe urine, fawn urine, doe in heat urine, elk urine, moose urine, goat urine, sheep urine, cow urine, horse urine, pig urine, goat urine and buffalo urine, the urine comprising 5.0 to 90.0% by weight of the composition.

* * * * *